(12) United States Patent
Cohen

(10) Patent No.: US 6,355,680 B1
(45) Date of Patent: Mar. 12, 2002

(54) ALBUMIN-BINDING COMPOUNDS THAT PREVENT NONENZYMATIC GLYCATION AND THAT MAY BE USED FOR TREATMENT OF GLYCATION-RELATED PATHOLOGIES

(75) Inventor: Margo P. Cohen, New York, NY (US)

(73) Assignee: Exocell, Inc., Philadelphia, PA (US)

( * ) Notice: Subject to any disclaimer, the term of this patent is extended or adjusted under 35 U.S.C. 154(b) by 0 days.

(21) Appl. No.: 09/349,853

(22) Filed: Jul. 8, 1999

Related U.S. Application Data

(63) Continuation-in-part of application No. 09/015,148, filed as application No. PCT/US97/02622 on Feb. 18, 1997, now Pat. No. 6,001,875, and a continuation-in-part of application No. 08/603,147, filed on Feb. 20, 1996, now abandoned.

(51) Int. Cl.$^7$ ............................................... A01N 37/12
(52) U.S. Cl. ........................ 514/534; 514/538; 514/570
(58) Field of Search ................................. 514/534, 538, 514/750

(56) References Cited

PUBLICATIONS

The Merck Index, Eleventh Edition, 1989, p. 3071, 1989.*
Amelioration of Diabetic Nephropathy by Treatment With Monoclonal Antibodies Against Glycated Albumin, Margo P. Cohen, Elizabeth Hud, and Van–Yu Wu, Kidney International, vol. 45 (1994), pp. 1673–1679.
Albumin Modified by Amadori Glucose Adducts Activates Mesangial Cell Type IV Collagen Gene Transcription, Margo P. Cohen, Elizabeth Hud, Van–Yu Wu and Fuad N. Ziyadeh, Molecular and Cellular biochemistry 151:61–67, 1995.
Prevention of Diabetic Nephropathy in db/db Mice With Glycated Albumin Antagonists, Margo P. Cohen, Kumar Sharma, Yulin Jin, Elizabeth Hud, Van–Yu Wu John Tomaszewski and Fuad N. Ziyadeh, J. Cllin. Invest, vol. 95, May 1995–2338–2345.
Effects of Glycated Albumin on Mesangial Cells: Evidence for a Role in Diabetic Nephropathy, Fuad N. Ziyadeh and Margo P. Cohen, Molecular and Cellular Biochemistry 125: 19–25, 1993.
Glycated Albumin Stimulates Fibronectin Gene Expression in Glomerular Mesangial Cells: Involvement of the Transforming Growth Factor–β System, Fuad N. Ziyadeh, Dong Cheol Han, Jonathan A. Cohen, Jia Guo, and Margo P. Cohen, Kidney International, vol. 53 (1998), pp. 631–638.
Amadori Glucose Adducts Modulate Mesangial Cell Growth and Collagen Gene Expression, Margo P. Cohn and Fuad N. Ziyadeh, Kidney International, vol. 45 (1994), pp. 475–484.
Prevention of Decline in Renal Function in the Diabetic db/db Mouse, M.P. Cohen, R.S. Clements, J.A. Cohen and C.W. Shearman, Diabetologia (1996)39:270–274.
Anti–Glycated Albumin Albumin Therapy Ameliorates Early Retinal Microvascular Pathology in db/db Mice, Rex S. Clements, Jr., W. Gerald Robison, Jr. and Margo P. Cohen, Journal of Diabetes and Its Complications 12:28–33.
Glycation of Human Serum Albumin: Inhibition by Diclofenac, Martinus A.M. van Boekel, Paul J.PC. van den Bergh and Herman J. Hoenders, Biochim, Biophys. Acta Protein Structure. Mol. Enzymol, (1992) 1120/2 (201–204).

* cited by examiner

*Primary Examiner*—Zohren Fay
(74) *Attorney, Agent, or Firm*—Caesar, Rivise, Bernstein, Cohen & Pokitilow, Ltd.

(57) ABSTRACT

The present invention is directed to compositions that inhibit the nonenzymatic glycation of albumin,, as well as methods of using compounds that inhibit albumin glycation for the treatment of glycation-related pathologies.

9 Claims, No Drawings

ALBUMIN-BINDING COMPOUNDS THAT PREVENT NONENZYMATIC GLYCATION AND THAT MAY BE USED FOR TREATMENT OF GLYCATION-RELATED PATHOLOGIES

RELATED APPLICATIONS

This application is a continuation-in-part application of application Ser. No. 08/603,147 filed on Feb. 20, 1996, entitled "Prevention of Albumin Glycation and Complications of Diabetes with Albumin-Binding Compounds", now abandoned, and of application Ser. No. 09/015,148, filed on Jan. 29, 1998, entitled "In vivo Methods of Treatment to Prevent Kidney Dysfunction using Substances that Inhibit Albumin Glycation", which matured into U.S. Pat. No. 6,001,875 which is a 371 of PCT/US97/02622 filed Feb. 18, 1997.

TECHNICAL FIELD OF INVENTION

The present invention is directed to the discovery of compositions that inhibit the nonenzymatic attachment of glucose to albumin, preventing the formation of glycated albumin. The compounds are useful in preventing and treating disorders of the kidney and other organs that result from deleterious effects of glycated albumin.

BACKGROUND OF THE INVENTION

Glycated albumin, which is formed by the condensation of glucose with reactive protein amino groups, adversely affects capillary function, structure and metabolism. Experimental studies have shown that this glycated protein has distinct biologic effects that the nonglycated counterpart does not possess. These effects include facilitated transport across capillary filtration barriers and hyperfiltration in the kidney, and stimulation of nitric oxide synthase and nitric oxide production, increased synthesis of extracellular matrix proteins, and activation of cytokine and growth factor systems in kidney and vascular tissue. These and other biologic effects of glycated albumin have been described in numerous scientific publications including *Kidney International* 42:875–881, 1992; *Lab Investigation* 51:27–35, 1997; *Kidney International* 45:475–484, 1994; *Molecular & Cellular Biochemistry* 125:19–25, 1993; *Molecular & Cellular Biochemistry* 151:61–67, 1995; *Kidney International* 53:631–638, 1998.

The described biologic activities are observed with concentrations of glycated albumin that found in clinical specimens from human subjects, and do not depend on elevated glucose concentrations to be operative. Since the circulating half-life of albumin in humans is 17 days, there is prolonged exposure of vascular beds to the glycated protein after it is formed.

The use of agents that block the effects of glycated albumin to ameliorate vascular pathologies has been explored in several scientific studies (*Kidney International* 45:1673–1679, 1994; *Journal of Clinical Investigation* 95:2338–2345, 1995; *Diabetologia* 39:270–274, 1996; *Journal of Diabetic Complications* 12:28–33, 1998). Such agents may be monoclonal antibodies or other molecules that react specifically with fructosyllysine residues that are present on glycated albumin but are not present on nongly- cated albumin, and which are disclosed in U.S. Pat. Nos. 5,223,392 and 5,518,720, incorporated by reference herein. Such therapies have been shown, among other things, to prevent the structural and functional changes characteristic of renal and retinal microvascular disease. Anti-glycated albumin therapy therefore has been proposed as a treatment modality for vascular pathologies.

A novel approach to prevent pathologies related to the biologic effects of glycated albumin would be to reduce the formation of the glycated protein and to lower its concentration in the circulation. This could be accomplished by administering compounds that, by binding to specific sites in albumin, can inhibit the attachment of glucose to physiologically important lysine amino groups. The compounds would achieve this desired effect by obscuring the reactive lysine amino group and/or causing a conformational shift in the tertiary structure of the albumin molecule that renders the important glycatable site inaccessible.

Identification of compounds which prevent glycation at physiologically important sites is difficult to accomplish and has not been described in the art. In vitro glycation is distinctly different from in vivo glycation. Excessive concentrations of glucose or reducing carbohydrate are used, and the number of sites that undergo glycation is significantly increased relative to sites which are subject to glycation in vivo. Physiologically important sites are only a small subset of the total number of sites and cannot be distinguished from the unimportant ones after in vitro glycation according to methods described in the art.

Binding to albumin is a likely prerequisite for a compound to prevent glycation of albumin and many compounds of diverse structural classes have been shown to bind to albumin at various sites. Examples include: vitamin C, vitamin E, vitamin $B_6$, diclofenac, acetylsalicylic acid, warfarin, bilirubin, iodobenzoic acids, diazepam, digitoxin, clofibrate, methotrexate, lithium, phenobarbital, cyclosporin benzodiazepine, paracetamol, ibuprofen, suprofen, aminodarone, propanolol, griseofulvan, and others. But binding to albumin is not sufficient for antiglycation activity. Only a few compounds have been reported to influence the condensation of carbohydrate with reactive protein amino groups in vitro, and none of them have been shown to affect lysine amino groups that are physiologically important in vivo or to be of therapeutic benefit when administered in vivo with respect to glycation-related pathologies (*Biochemical & Biophysical Research Communications* 165:991–996, 1988; *Life Sciences* 43:1725–1731, 1988; *Diabete & Metabolisme* 14:40–42, 1988; *Biochemica et Biophysica Acta* 1120:201–204, 1992; *Diabetes* 41:167–173, 1992). Moreover, the conditions employed in such in vitro studies are irrelevant to in vivo conditions as to degree of glycation, the reducing sugar and concentration used, and the concentration of compound tested. Binding to albumin and inhibition of in vitro glycation is not synonymous with prevention of glycation at physiologically important sites.

It is a finding of the present invention that many compounds bind to albumin and inhibit glycation at unimportant sites but do not prevent glycation at physiologically important sites.

It is another finding of the present invention that agents that bind to fructosyllysine residues on albumin and, in so doing, prevent pathobiologic effects of glycated albumin provide a useful tool for elucidating which albumin binding ligands are potentially important in preventing the formation of glycated sites that are pathophysiologically important.

The present invention is directed toward discovery of albumin-binding compounds that block non-enzymatic glycation of physiologically important sites which, when glycated, lead to vascular pathologies. The present invention is further directed to methods of use of these novel agents for the treatment of glycation-related pathologies, and novel methods of synthesis of these agents.

SUMMARY OF THE INVENTION

The present invention provides novel compounds that inhibit the nonenzymatic glycation of albumin at physiologically relevant sites.

The present invention also provides improved methods of synthesis of 2-phenylamino-phenylacetic acid derivatives.

The present invention further provides novel compositions for preventing and treating glycation-induced pathologies.

These and other objects of the invention are achieved with the discovery of compounds that are reactive with domain(s) in human albumin that are susceptible to nonenzymatic glycation in vivo; that, by binding to the sites in the structure of albumin, protect the protein from attachment to glucose.

DETAILED DESCRIPTION

The present invention evolved from the finding that glycation-associated pathologies can be ameliorated by ligand compounds that bind to specific glycated sites on albumin. A novel finding of the present invention is that these ligands can be used to identify other compounds that prevent glycation of pathophysiologically important sites in the albumin molecule that are selectively subject to glycation in vivo and that, when glycated, cause deleterious biologic effects in relevant tissues. The present invention further finds that these compounds can be identified by their ability to prevent, in their binding to albumin, the formation of fructosyllysine epitopes in glycated albumin that are recognized by monoclonal antibodies that are site selective for fructosyl-lysine residues that are known to be involved in glycation-associated pathologies.

It is a finding of the present invention that compounds are identified that, by binding to human albumin and protecting the protein from nonenzymatic glycation at pathophysiologically important sites, are therapeutically useful for the treatment of glycation-related pathologies.

Compounds of the present invention are capable of binding to sites in the primary structure of albumin which contain a lysine residue that is a preferential site of nonenzymatic glycation in vivo and/or cause a conformational shift in the tertiary structure of the protein, rendering the glycatable site inaccessible to glucose attachment.

Compounds which are potentially useful are those which are capable of binding albumin and include but are not limited to: vitamin C, vitamin E, vitamin $B_6$, diclofenac, acetylsalicylic acid, warfarin, bilirubin, iodobenzoic acids, diazepam, digitoxin, clofibrate, methotrexate, lithium, phenobarbital, cyclosporin benzodiazepine, paracetamol, ibuprofen, suprofen, aminodarone, propanolol, griseofulvan, and others.

A subset of therapeutically useful compounds can be identified with the monoclonal antibody A717 which binds to fructosyl-lysine residues on albumin and, in so doing, blocks the effects of glycated albumin on vascular pathology. Compounds which prevent the formation of glycated sites recognized by A717 will be therapeutically useful.

Compounds of the present invention possessing this activity are of the structural formula:

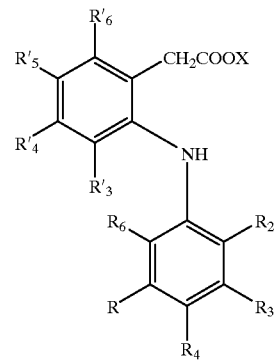

wherein: X is hydrogen, sodium, lithium or potassium and $R'_3, R'_4, R'_5, R'_6, R_2, R3, R_4, R_5, R_6$ are the same or different and are hydrogen, chlorine, bromine, fluorine, iodine, methyl, ethyl, propyl, isopropyl, butyl, pentyl, butyloxy, pentyloxy, cyano, thio, methoxy, ethoxy, hydroxy, phosphate, sulfate, nitrate, or amino.

The compounds of the present invention can be tested and selected for low cyclo-oxygenase inhibitory activity and high anti-glycation activity, since some compounds of this structural class have been associated with cyclo-oxygenase inhibitory activity. It is a finding of this invention that this property confers therapeutic advantage by achieving potent inhibition of albumin glycation and lessening untoward side-effects of cyclo-oxygenase inhibition when administered in vivo.

The compounds of the present invention are capable of preventing cellular and tissue damage that is evoked by glycated albumin that is present in the circulation. Since therapeutic concentrations of the compounds of the present invention can inhibit the formation of glycated albumin with high $IC_{50}$ (the concentration giving 50% inhibition) ratios of anti-glycation to cyclo-oxygenase inhibitory activities, the present invention provides a novel and improved method for the treatment of glycation-related pathologies.

The compounds of this structural class (2-(phenylamino) phenylacetic acids) can be produced following the methods outlined in schemes 1–6. Scheme 1 describes the synthesis of substituted diphenylamines and the subsequent condensation of the appropriate diphenylamines with refluxing chloracetyl chloride to yield the substituted 2-chloro-N-phenylacetanilides. Cyclization is achieved by heating at 160° C. in a melt with $AlCl_3$. Hydrolysis of the substituted N-aryloxindoles with NaOH in refluxing ethanolic solution followed by acidification gives the 2-(phenylamino) phenylacetic acids.

Scheme I

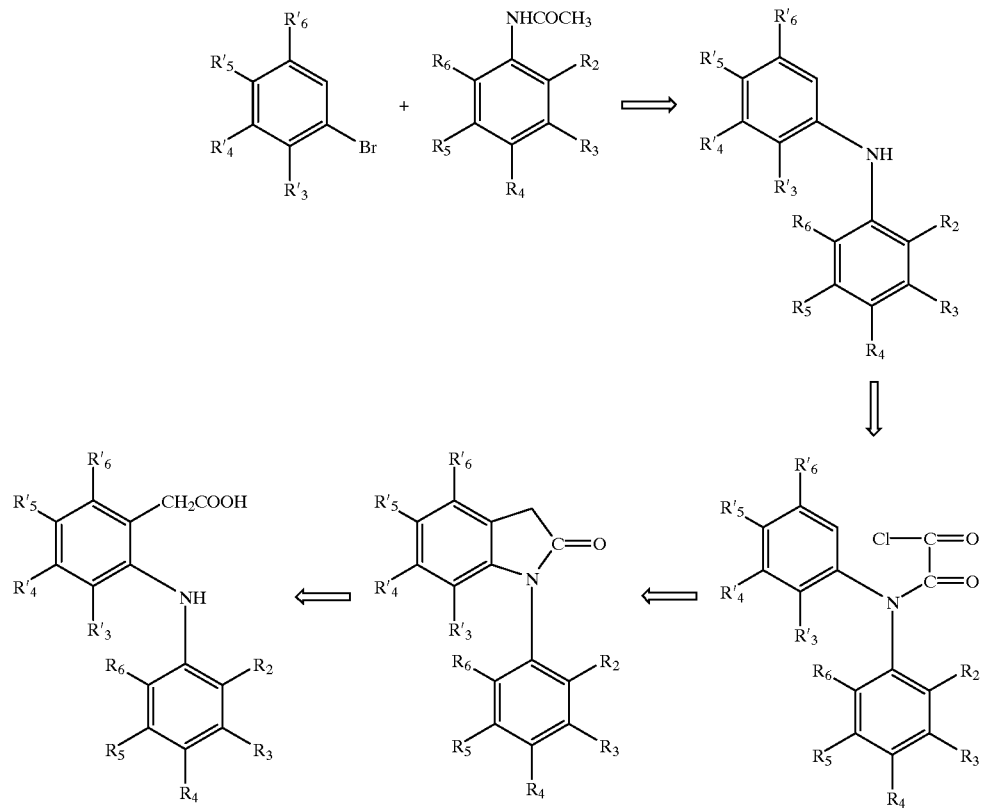

Since alkyl migration and splitting of alkoxy groups can occur during the cyclization reaction above, scheme 2 is beneficial in certain cases. In this scheme substituted diphenylamines are treated with oxalyl chloride in benzene followed by cyclization of the N-phenyloxamic acid chloride with $AlCl_3$ in tetrachloroethane to yield N-arylisatins. Hydrolysis and acidification gives the corresponding phenylglyoxylic acids which are then reduced and acidified to produce the 2-(phenylamino) phenylacetic acids.

Scheme 2

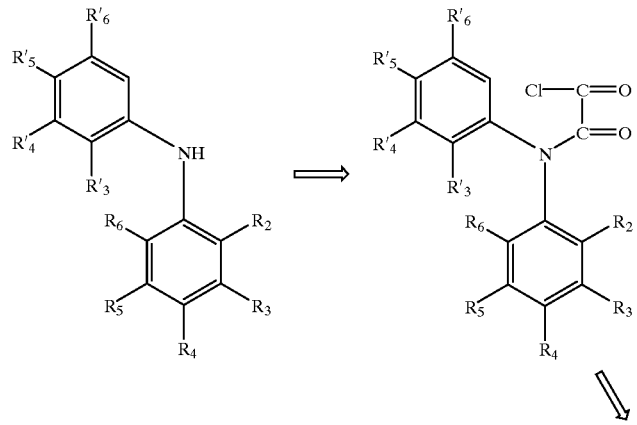

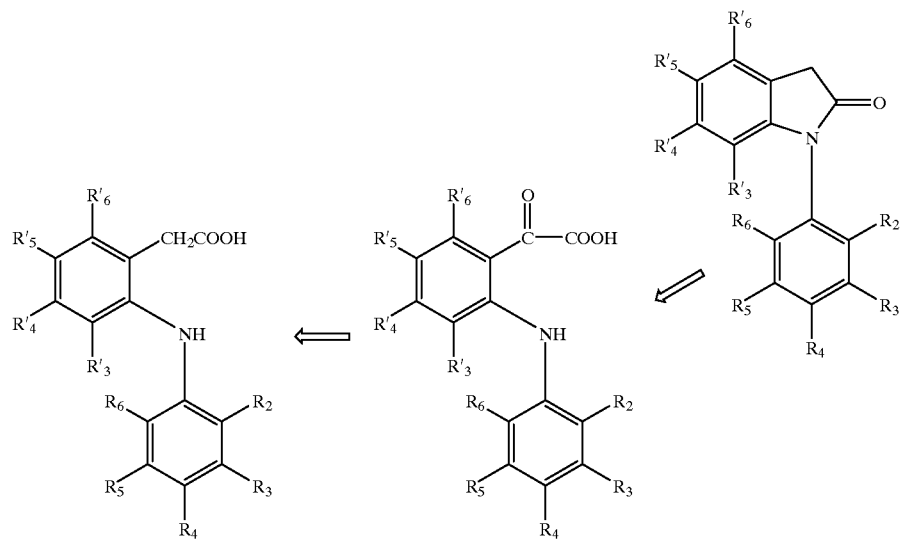

Schemes 1 and 2 are general routes to 2-(phenylamino) phenyl acetic acids, provided that both ortho positions of one phenyl ring of the diphenylamines are occupied in order to avoid the formation of positional isomers of the intermediate oxindoles and isatins. Schemes 3 and 4 are synthetic routes that avoid the formation of isomers. In scheme 3, potassium 2-iodophenyl acetate is reacted with substituted anilines in the presence of potassium carbonate and activated copper powder in hot N-methyl-2-pyrrolidone. Acidification and crystallization yields the 2-(phenylamino) phenylacetic acids.

Scheme 3

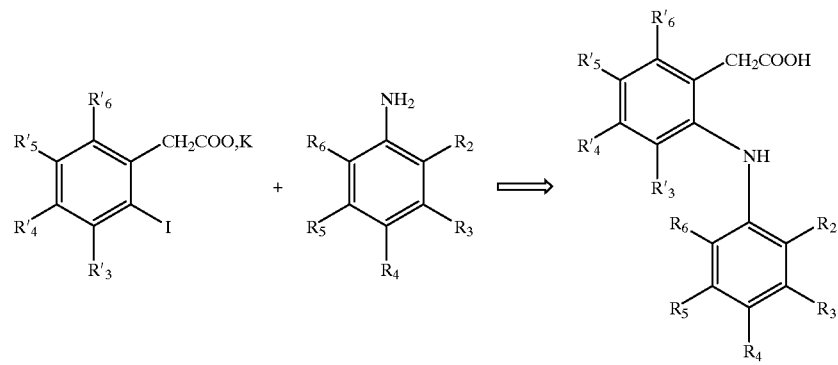

Scheme 4 involves the condensation of N,N-dimethyl-2-iodophenylacetamide and anilines in the presence of anhydrous potassium carbonate, copper, and cuprous iodide in refluxing toluene to give the substituted N,N-dimethyl-2-(phenylamino) phenylacetamides. Hydrolysis with KOH in refluxing ethanol followed by acidification yields the 2-(phenylamino) phenylacetic acids.

Scheme 4

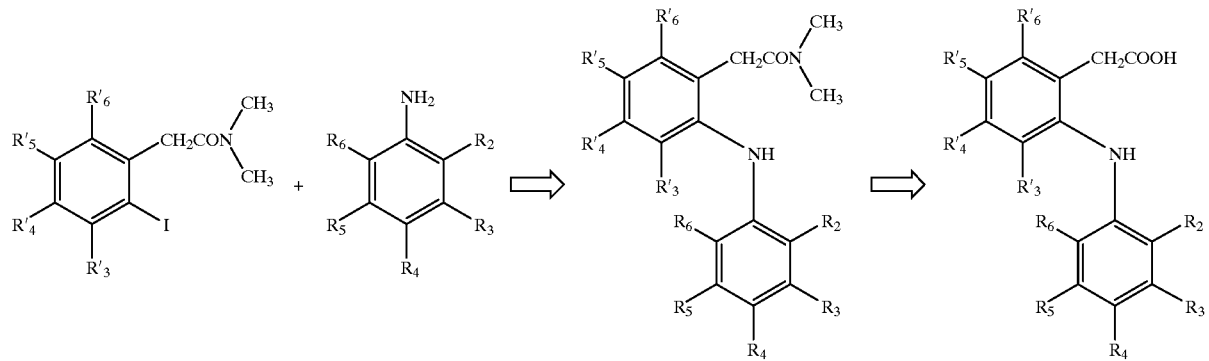

Hydroxylated 2-(phenylamio) phenylacetic acids are synthesized from the appropriately substituted methoxy-2-(phenylamino) phenylacetic acids (prepared by scheme 2 and 4). In scheme 5, the methoxy-derivatives are treated with pyridine hydrochloride at 170° C. which gives the hydroxy substituted N-phenyloxindoles. Hydrolysis with NaOH in refluxing N-butanol completes the synthesis.

Scheme 5

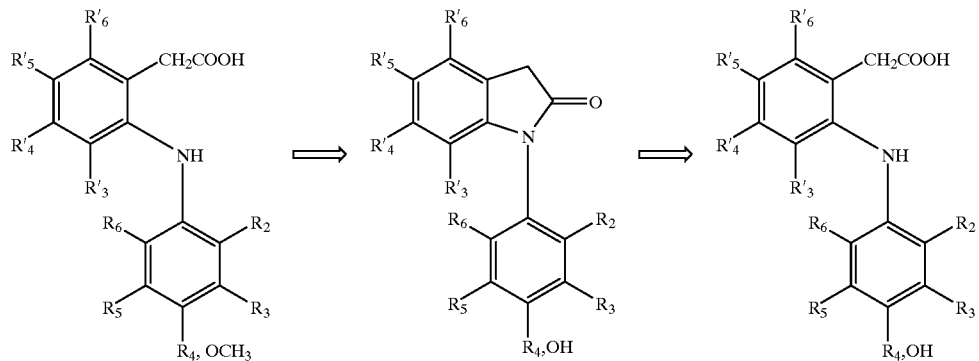

Hydroxylated compounds with additional methoxy groups are prepared by hydrogenation of he corresponding benzyloxy analogues with Pd-C in tetrahydrofuran and 1,2-dichlorobenzene (scheme 6).

Scheme 6

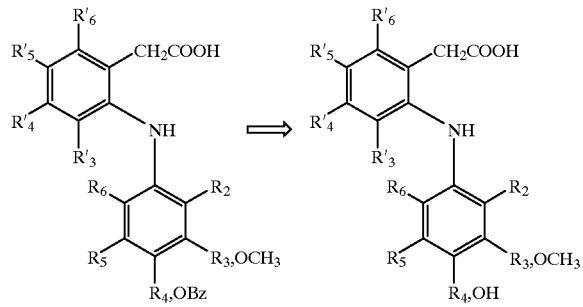

Scheme 7

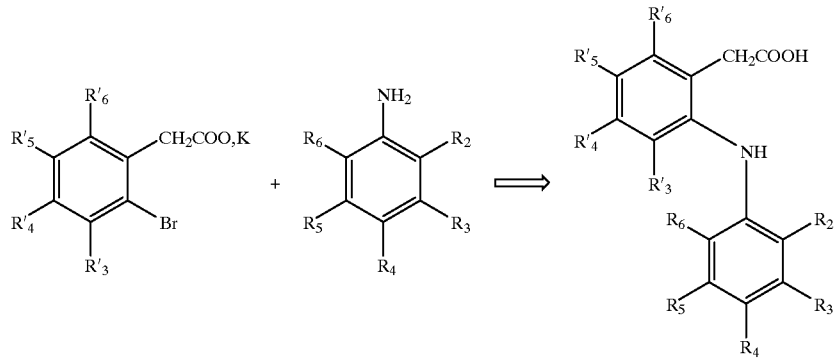

This invention provides an improved method of synthesis of 2-(phenylamino) phenylacetic acids. Analogous to schemes 3 and 4, scheme 7 produces the 2-(phenylamino) phenylacetic acid from a direct condensation of a phenylacetic acid with an aniline. In this scheme, the phenylacetic acid contains a reactive bromine, the amount of aniline is reduced, the reaction time is reduced, the potassium carbonate is reduced to prevent oxidation of the reaction products, the N-methylpyrrolidone is reduced to accelerate the bimolecular reaction, and reduced amounts of freshly prepared, activated copper is used. This method improved yields of the desired product with little formation of oxyindoles or oxidation products.

This invention also provides therapeutic compositions comprising the above-described compounds.

This invention further provides a method for treating disease comprising administering to the patient an effective amount of a therapeutic composition comprised of the above-described compound(s) capable of inhibiting albumin glycation and a pharmaceutically acceptable carrier therefor.

The present invention also comprises one or more compounds as described above formulated into compositions together with one or more non-toxic physiologically acceptable carriers, adjuvants or vehicles which are collectively referred to herein as carriers, for parenteral injection for oral administration in solid or liquid form, for rectal or topical administration, or the like. The compositions can be administered to humans either orally, rectally, parenterally (intravenously, intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifuingal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents delaying absorption, for example, aluminum monostearate and gelatin.

Solid dosage forms for oral administration include capsules, tablets, pills, powders and granules. In such solid dosage forms, the active compound is admixed with at least one inert customary, pharmaceutically acceptable, excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glycerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as for example, quaternary ammonium compounds, (g) wetting agents, as for example, cetyl alcohol and glycerol monostearate, (h) adsorbents, as for example, kaolin and bentonite, and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like. Solid dosage forms such as tablets, capsules, pills and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes.

The active compounds can also be in microencapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyethylene sorbitol and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays and inhalants. The active component is admixed under sterile conditions with a physiologically acceptable carrier and any preservatives, buffers or propellants as may be required. Ophthalmic formulations, eye ointments, powders and solutions are also contemplated as being within the scope of this invention.

Actual dosage levels of active ingredients in the compositions of the present invention may be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors.

The total daily dose of the compounds of this invention administered to a host in single or divided dose may be in amounts, for example, of from about 1 nanomol to about 100 micromols per kilogram of body weight. Dosage unit compositions may contain such amounts or such submultiples therefor as may be used to make up the daily dose. It will be understood, however, that the specified dose level for any particular patient will depend upon a variety of factors including the body weight, general health, sex, diet, time and route of administration, rates of absorption and excretion, combination with other drugs and the severity of the particular disease being treated. The dosage level may also depend on patient response as determined by measurement of the concentration of glycated albumin in the circulation at suitable intervals after administration.

The above disclosure generally describes the present invention. A more complete understanding can be obtained by reference to the following specific examples which are provided herein for purposes of illustration only, and are not intended to limit the scope of the invention.

EXAMPLE 1

Identification of Compounds which Prevent the Glycation of Pathophysiologically Important Sites that are Subject to Glycation In vivo Human albumin (10 mg/ml) was incubated for 4 days in buffered saline in the presence of 0 or 40 mM glucose, with or without the test compound (1–1000 $\mu$M). After dialysis to remove free glucose and compound, the amount of glycated albumin formed was determined by enzyme-linked immunosorbent assay using monoclonal antibodies known to specifically react with Amadori-glucose adducts in glycated albumin and to be unreactive with the nonglycated protein (ATCC HB 9596; U.S. Pat. No. 5,223,392), incorporated by reference herein. In vivo administration of this anti-glycated albumin antibody is also known to prevent the adverse biologic effects of glycated albumin. The performance of paired incubations allowed comparison of the amount of glycated albumin formed under control (0 mM glucose), stimulated (40 mM glucose) and inhibited (test compound plus glucose) conditions. From these data, compounds were identified which inhibit the formation of fructosyllysine epitopes in albumin at lysine amino sites that are subject to glycation in vivo and that are important for the biologic activity of glycated albumin. A representative sample of test compounds from different structural classes is shown in Table 1.

TABLE 1

Prevention of Albumin Glycation at Physiologically Significant Sites Of these compounds, 2-[3-chlorophenyl) amino] phenylacetic acid

| Compound | Class | IC$_{50}$ for Albumin Glycation ($\mu$M) |
|---|---|---|
| 2-[3-chlorophenyl) amino]-benzene acetic acid | Heteroaryl acid | 15 |
| 1-methyl-5-[p-toluoyl]pyrrole-2-acetic acid | Heteroaryl acetic acid | 11.5 × 10$^4$ |
| 4-hydroxy-2-methyl-3-pyrid-[2-yl-carbamoyl]1H-1,2 benzothiazine 1,1-dioxide | Enolic acid | >10$^6$ |
| 2-[(2,6-dichloro-3-methyl-phenyl)-amino]benzoic acid | Anthranilic acid | >10$^6$ |
| α-methyl-4-[2-methyl)propyl)] benzene acetic acid | Aryl propionic acid | 7.8 × 10$^4$ |
| 1-[p-chlorobenzoyl]-methoxy-2-methylindole-3-acetic acid | Indole acetic acid | 2.7 × 10$^4$ |

TABLE 1-continued

Prevention of Albumin Glycation at Physiologically Significant Sites Of these compounds, 2-[3-chlorophenyl) amino] phenylacetic acid

| Compound | Class | $IC_{50}$ for Albumin Glycation ($\mu$M) |
| --- | --- | --- |
| [Z]-5-fluoro-2-methyl-1 [p-(methylsulfinyl)phenyl] (methylene-1H-indene-3-acetic acid | Indole acetic acid | $2.2 \times 10^4$ |

Of these compounds, 2-[(2,6-dichlorophenyl)amino] phenylacetic acid showed the greatest ability to prevent glycation of the physiologically important sites that are recognized by the site-specific antibodies reactive with fructosyllysine residues that are formed in vivo as a result of nonenzymatic glycation.

EXAMPLE 2

Improved Synthesis of 2-(phenylamino)phenylacetic acids

One molar equivalent of bromophenylacetic acid or its cationic salt, two equivalents of an appropriately substituted aniline, and two equivalents of anhydrous potassium carbonate were mixed with 3 ml of N-methyl pyrrolidine and to this mixture 7 mole percent of freshly prepared activated copper was added. The reaction mixture was heated at 115–120° C. for 4 hours. The resulting slightly grayish mixture was filtered hot over a bed of Celite and the Celite was washed with water (200 ml) and hexane (200 ml). The filtrate was transferred to a separating funnel and extracted with hexane. The aqueous layer was cooled to 5° C. and neutralized with dilute hydrochloric acid (1:3) which also was kept at 5° C. The precipitated product was filtered, thoroughly washed with water, and dried under suction (30% yield based on bromophenylacetic acid).

This protocol for successful synthesis of the desired compound departs from described procedures and provides improved methods for synthesis of substituted anilines. Protocols described in the art employ 1 equivalent of bromophenylacetic acid, 5 equivalents of the aniline, 4 equivalents of anhydrous potassium carbonate, and 1 equivalent of copper powder, that are mixed and refluxed in 30 ml methyl pyrrolidine for 20 hours at 120° C., followed by treatment with hot water and then chloroform to precipitate the potassium salt of the anilinophenylacetic acid. Application of the prior art methods yielded tarry reaction products that failed to form any precipitate, contained several compounds, and showed only a trace of the desired compound. The improved method of synthesis a) reduces reaction time to 4 hours; b) maintains reaction temperature between 115–120° C.; c) reduces the amount of aniline to two equivalents per equivalent of bromophenylacetic acid; d) reduces the potassium carbonate to two equivalents (one to neutralize the bromo acid and one for neutralizing the hydrobromic acid generated in the reaction), since excess potassium carbonate caused base-catalyzed oxidation of the reaction products; e) reduces the amount of N-methyl pyrrolidine 10 fold to accelerate the bimolecular reaction and enable isolation of the final product; and f) uses freshly activated copper instead of copper powder, and reduces the amount to 7 mole percent of the bromophenylacetic acid used.

EXAMPLE 3

Synthesis of 2-[(phenyl)amino]phenylacetic acid 2-bromophenylacetic acid (25 mmol) was added to a mixture of 50 mmol of aniline, 50 mmol of anhydrous potassium carbonate, (7%) mmol of activated copper powder, and 3 ml of N-methylpyrrolidone at 120° C. The mixture was kept at 120° C. for 4 h with stirring. The resulting slightly grayish mixture was filtered while hot through a bed of Celite and the Celite was washed with water (200 ml) and hexane (200 ml). The filtrate was transferred to a separating funnel and extracted with hexane and cooled to room temperature. The aqueous layer was removed, cooled to 5° C., and neutralized with dilute hydrochloric acid (1:3) which was also kept at 5° C. The precipitated 2-[(phenyl)amino]phenylacetic acid was collected by filtration, thoroughly washed with water, and dried under suction.

EXAMPLE 4

Synthesis of 2-[(2-chlorophenyl)amino]phenylacetic acid

In the manner described in example 3, 2-bromophenylacetic acid was condensed with 2-chloroaniline to yield 2-[(2-chlorophenyl)amino] phenylacetic acid.

EXAMPLE 5

Synthesis of 2-[(3-chlorophenyl)amino]phenylacetic acid

In the manner described in example 3, 2-bromophenylacetic acid was condensed with 3-chloroaniline to yield 2-[(3-chlorophenyl)amino] phenylacetic acid.

NMR (DM 50-$d_6$): $CH_2$ singlet at 3.7 ppm; appropriate aromatic protons with proper chemical shift; acid proton at 13 ppm Elemental Analysis: $C_{14}H_{12}ClNO_2$ (acid); $C_{14}H_{11}ClNO_2Na$ (salt)

TLC: Single spot

Melting point: 102–103° C.

EXAMPLE 6

Synthesis of 2-[(4-chlorophenyl)amino]phenylacetic Acid

In the manner described in example 3, 2-bromophenylacetic acid was condensed with 4-chloroaniline to yield 2-[(4-chlorophenyl)amino] phenylacetic acid.

EXAMPLE 7

Synthesis of 2-[(2,3-dichlorophenyl)amino] phenylacetic acid

In the manner described in example 3, 2-bromophenylacetic acid was condensed with 2,3-dichloroaniline to yield 2-[(2,3-dichlorophenyl)amino] phenylacetic acid.

EXAMPLE 8

Synthesis of 2-[(2,4-dichlorophenyl)amino] phenylacetic Acid

In the manner described in example 3, 2-bromophenylacetic acid was condensed with 2,4-dichloroaniline to yield 2-[(2,4-dichlorophenyl)amino] phenylacetic acid.

EXAMPLE 9

Synthesis of 2-[(2,5-dichlorophenyl)amino]phenylacetic Acid

In the manner described in example 3, 2-bromophenylacetic acid was condensed with 2,5-dichloroaniline to yield 2-[(2,5-dichlorophenyl)amino]phenylacetic acid.

EXAMPLE 10

Synthesis of 2-[(3,4-dichlorophenyl)amino]phenylacetic Acid

In the manner described in example 3, 2-bromophenylacetic acid was condensed with 3,4-dichloroaniline to yield 2-[(3,4-dichlorophenyl)amino]phenylacetic acid.

EXAMPLE 11

Synthesis of 2-[(3,5-dichlorophenyl)amino]phenylacetic Acid

In the manner described in example 3, 2-bromophenylacetic acid was condensed with 3,5-dichloroaniline to yield 2-[(3,5-dichlorophenyl)amino]phenylacetic acid.

EXAMPLE 12

Synthesis of 2-[(2,6-dimethylphenyl)amino]phenylacetic Acid

In the manner described in example 3, 2-bromophenylacetic acid was condensed with 2,6-dimethylaniline to yield 2-[(2,6-dimethylphenyl]amino]phenylacetic acid.

EXAMPLE 13

Synthesis of 2-[(2,3-dimethylphenyl)amino]phenylacetic Acid

In the manner described in example 3, 2-bromophenylacetic acid is condensed with 2,3-dimethylaniline to yield 2-[(2,3-dimethylphenyl)amino]phenylacetic acid.

EXAMPLE 14

Synthesis of 2-[(2,4-dimethylphenyl)amino]phenylacetic Acid

In the manner described in example 3, 2-bromophenylacetic acid is condensed with 2,4-dimethylaniline to yield 2-[(2,4-dimethylphenyl)amino]phenylacetic acid.

EXAMPLE 15

Synthesis of 2-[(2,5-dimethylphenyl)amino]phenylacetic Acid

In the manner described in example 3, 2-bromophenylacetic acid is condensed with 2,5-dimethylaniline to yield 2-[(2,5-dimethylphenyl)amino]phenylacetic acid.

EXAMPLE 16

Synthesis of 2-[(3,4-dimethylphenyl)amino]phenylacetic Acid

In the manner described in example 3, 2-bromophenylacetic acid is condensed with 3,4-dimethylaniline to yield 2-[(3,4-dimethylphenyl)amino]phenylacetic acid.

EXAMPLE 17

Synthesis of 2-[(3,5-dimethylphenyl)amino]phenylacetic Acid

In the manner described in example 3, 2-bromophenylacetic acid is condensed with 3,5-dimethylaniline to yield 2-[(3,5-dimethylphenyl)amino]phenylacetic acid.

EXAMPLE 18

Synthesis of 2-[(2-methylphenyl)amino]phenylacetic Acid

In the manner described in example 3, 2-bromophenylacetic acid is condensed with o-toluidine to yield 2-[(2-methylphenyl)amino]phenylacetic acid.

EXAMPLE 19

Synthesis of 2-[(3-methylphenyl)amino]phenylacetic Acid

In the manner described in example 3, 2-bromophenylacetic acid is condensed with m-toluidine to yield 2-[(3-methylphenyl)amino]phenylacetic acid.

EXAMPLE 20

Synthesis of 2-[(4-methylphenyl)amino]phenylacetic Acid

In the manner described in example 3, 2-bromophenylacetic acid is condensed with p-toluidine to yield 2-[(4-methylphenyl)amino]phenylacetic acid.

EXAMPLE 21

Synthesis of 2-[(2,4,6-trichlorophenyl)amino]phenylacetic Acid

In the manner described in example 3, 2-bromophenylacetic acid is condensed with 2,4,6-trichloroaniline to yield 2-[(2,4,6-trichlorophenyl)amino]phenylacetic acid.

EXAMPLE 22

Synthesis of 2-[(2,6-dichloro-4-methoxyphenyl)amino]phenylacetic Acid

Oxalyl chloride (0.5 mol) was added dropwise at 5° C. to a solution of 2,6-dichloro-4-methoxydiphenylamine (0.25 mol) in 375 ml of benzene. The mixture was stirred for 2 h at room temperature and evaporated. The residue was dissolved in 400 ml of benzene and the solution was again evaporated to dryness to obtain N-(2,6-dichloro-4-methoxyphenyl) oxaniloyl chloride. This intermediate was dissolved in 600 ml of tetrachloroethane. $AlCl_3$ (40 g) was added slowly, and the mixture was stirred for 20 h at room temperature. The mixture was then poured over 200 ml of 2N HCl containing 800 g of ice. The organic phase was washed with water, 2N $KHCO_3$, again with water, and evaporated. Crystallization from ether yielded 1-(2,6-dichloro-4-methoxyphenyl) isatin. This intermediate was dissolved win 215 ml of 1N NaOH and 2100 ml of ethanol and was heated under reflux for 10 min. The solution was cooled and evaporated. The residue was dissolved in 2000 ml of water, washed with ether, and acidified with 2N HC1. The precipitate was extracted with ether. The organic extract gave, after washing with water, evaporation and crystallization for ether, the product 2-[2,6-dichloro-4-methoxyphenyl)amino]glyoxylic acid. This intermediate (0.22 mol) was dissolved in 900 ml of 2-methoxyethanol. Hydrazine hydrate (1 mol) was added and the temperate of the mixture was increased to 60° C. NaOCH$_3$ (2.3 mol) was added slowly and the mixture was slowly heated to 150° C., whereby methanol, water, hydrazine, and part of the solvent evaporated. The mixture was kept at 150° C. for 1 h, collected, and poured over 8 kg of crushed ice. The aqueous phase was extracted with 800 ml of ether and acidified with concentrated HCl at 0° C. The precipitated oil was extracted with ether. The ether extract was washed with water and evaporated. The residue was crystallized from ether-petroleum ether to yielded 2-[2,6-dichloro-4-methoxyphenyl)amino]phenylacetic acid.

EXAMPLE 23

Synthesis of 2-[(2,6-dichloro-4-hydroxyphenyl) amino]phenylacetic Acid

The 2-[(2,6-dichloro-4-methoxyphenyl)amino] phenylacetic acid (0.1 mol) from example 22 was added in portions to a melt of 200 g of pyridine hydrochloride (1.75 mol) at 170° C. The mixture was heated at 180° C. for 3 h and poured onto 2000 ml of ice water while hot. The precipitated product was filtered off, washed with water, and dissolved in 1000 ml of ethyl acetate. The organic phase was washed with 200 ml of 1N HCl in water (2×100 ml) and evaporated to give N-(2,6-dichloro-4-hydroxyphenyl) oxindole. To a solution of 8 g of N-(2,6-dichloro-4-hydroxyphenyl)-oxindole in 200 ml of n-butanol were added 7 g of NaOH and 1 g of KOH, and the reaction mixture was refluxed for 24 h and evaporated in vacuo. The residue was dissolved in 700 ml of water and the aqueous solution was extracted with ether (2×200 ml), cooled to 0° C., and acidified with concentrated HCl. The precipitate was taken up in 300 ml of ether. The organic phase was washed with 30 ml of water, 0.5N NaHCO$_3$ (5×80 ml), and 80 ml of 2N KHCO$_3$ solution. The combined NaHCO$_3$ extracts were cooled to 0° C. and acidified with 2N HCl, and the precipitate was dissolved in 200 ml of ether. The organic layer was washed with 30 ml of water and evaporated to yield 2-[(2, 6-dichloro-4-hydroxyphenyl)amino]phenylacetic acid.

EXAMPLE 24

Synthesis of 2-[(2,6-dichloro-3-methoxyphenyl) amino]phenylacetic Acid

In the manner described in example 22, 2,6-dichloro-3-methoxydiphenylamine was used to produce 2-[(2,6-dichloro-3-methoxyphenyl)amino]phenylacetic acid.

EXAMPLE 25

Synthesis of 2-[(2,6-dichloro-3-hydroxyphenyl) amino]phenylacetic Acid

In the manner described in example 23, 2-[(2,6-dichloro-3-methoxyphenyl)amino]phenylacetic acid was converted to 2-[(2,6-dichloro-3-hydroxyphenyl)amino]phenylacetic acid.

EXAMPLE 26

Synthesis of 2-[(2,6-dichloro-3-methylphenyl) amino]phenylacetic Acid

A mixture of 2,6-dichloro-3-methyldiphenylamine (0.17 mol) and chloroacetyl chloride (0.5 mol) was refluxed for 16 h, cooled, and evaporated. The residue was dissolved in 500 ml of chloroform-ether (1:2). The organic phase was washed with 100 ml of 2N KHCO$_3$ and 100 ml of water and evaporated. The residue was recrystallized from MEOH to give 2-chloro-N-(2',6'-dichloro-3'-methylphenyl)-N-phenylacetamide. This intermediate (0.1 mol) and 30 g of AlCl$_3$ were mixed, and the mixture was heated at 160° C. for 2 h (melting occurs at 100° C.). The molten mass was cooled and poured onto 300 g of crushed ice while the mixture was stirred. The precipitated oil was dissolved in 300 ml of chloroform. The organic phase was washed with 50 ml of 2N KHO$_3$ and 50 ml of water and evaporated. Recrystallization from MEOH gave 1-(2,6-dichloro-3-methylphenyl) oxindole. A solution of 18.6 g of this intermediate, 66 ml of 2N NaOH, and 66 ml of EtOH was refluxed for 4 h. The clear solution was cooled in an ice bath for 4 h. The precipitated crystals were filtered off and recrystallized from 80 ml of water to yield 2-[(2,6-dichloro-3-methylphenyl)amino] phenylacetic acid.

EXAMPLE 27

Synthesis of 2-[(2,6-dichlorophenyl)amino]5'-methoxyphenylacetic Acid

In the manner described in example 22, 4'-methoxy-2,6-dichlorodiphenylamine was used to yield 2-[(2,6-dichlorophenyl)amino]5'-methoxyphenylacetic acid.

EXAMPLE 28

Synthesis of 2-[(2,6-dichlorophenyl)amino]5'-hydroxyphenylacetic Acid.

In the manner described in example 23, 2-[(2,6-dichlorophenyl)amino]5'-methoxyphenylacetic acid was converted to 2-[(2,6-dichlorophenyl)amino]5'-hydroxyphenylacetic acid.

EXAMPLE 29

Synthesis of 2-[(2-methyl-3-chlorophenyl)amino] phenylacetic Acid

In the manner described in example 3, 2-bromophenylacetic acid is condensed with 2-methyl-3-chloroaniline to yield 2-[2-methyl-3-chlorophenyl)amino] phenylacetic acid.

EXAMPLE 30

Synthesis of 2-[(2,6-dichlorophenyl)amino]6'-bromophenylacetic Acid

In the manner described in example 26, 5-bromo-2',6'-dichlorodiphenylamine is used to yield 2-[(2,6-dichlorophenyl)amino]6'-bromophenylacetic acid.

EXAMPLE 31

Synthesis of 2[(2-chloro-3-methylphenyl)amino] phenylacetic Acid

In the manner described in example 3, 2-bromophenylacetic acid is condensed with 2-chloro-3-methylaniline to yield 2-[(2-chloro-3-methylphenyl)amino] phenylacetic acid.

EXAMPLE 32

Synthesis of 2-[(2-chloro-6-fluorophenyl)amino] phenylacetic Acid

In the manner described in example 26, 2-chloro-6-fluorodiphenylamine is used to yield 2-[(2-chloro-6-fluorophenyl)amino]phenylacetic acid.

EXAMPLE 33

Synthesis of 2-[(2,3,5,6-tetramethylphenyl)amino] 5'-chlorophenylacetic Acid

In the manner described in example 22, 4-chloro-2',3', 5'6'-tetramethyldiphenylamine is used to yield 2-[(2,3,5,6-tetramethylphenyl)amino]5'-chlorophenylacetic acid.

EXAMPLE 34

Synthesis of 2-[(2,6-diethylphenyl)amino] phenylacetic Acid

In the manner described in example 3, 2-bromophenylacetic acid is condensed with 2,6-diethylaniline to yield 2-[(2,6-diethylphenyl)amino] phenylacetic acid.

EXAMPLE 35

Synthesis of 2-[(2,4-difluorophenyl)amino] phenylacetic Acid

In the manner described in example 3, 2-bromophenylacetic acid was condensed with 2,4-difluoroaniline to yield 2-[(2,4-difluorophenyl)amino] phenylacetic acid.

EXAMPLE 36

Synthesis of 2-[(2,6-difluorophenyl)amino] phenylacetic Acid

In the manner described in example 3, 2-bromophenylacetic acid was condensed with 2,6-difluoroaniline to yield 2-[(2,6-difluorophenyl)amino] phenylacetic acid.

EXAMPLE 37

Synthesis of 2-[(2,6-dichloro-3-methoxy-4-benzyloxyphenyl)amino]phenylacetic Acid In the manner described in example 22, 2,6-dichloro-3-methoxy-4-benzyloxydiphenylamine was used to yield 2-[(2,6-dichloro-3-methoxy-4-benzyloxyphenyl)amino] phenylacetic acid.

EXAMPLE 38

Synthesis of 2-[(2,6-dichloro-3-methoxy-4-hydroxyphenyl)amino]phenylacetic Acid

The 2-[(2,6-dichloro-3-methoxy-4-benzyloxyphenyl) amino]phenylacetic acid (10 g) from example 37 was hydrogenated with Pd-C (1 g, 5%) in tetrahydrofuran (100 ml) and 1,2-dichlorobenzene (10 ml) at normal pressure for 25 min at room temperature. The catalyst was removed by filtration, and the filtrate was evaporated to leave the final product 2-[(2,6-dichloro-3-methoxy-4-hydroxyphenyl)amino] phenylacetic acid.

EXAMPLE 39

Synthesis of 2-[(2,6-dichlorophenyl)amino]6'-methoxyphenylacetic Acid

In the manner described in example 22, 5-methoxy-2',6'-dichlorodiphenylamine was used to yield 2-[(2,6-dichlorophenyl)amino]6'-methoxyphenylacetic acid.

EXAMPLE 40

Synthesis of 2-[(2,6-dichlorophenyl)amino]6'-hydroxyphenylacetic Acid

In the manner described in example 23, 2-[(2,6-dichlorophenyl)amino]6'-methoxyphenylacetic acid was converted to 2-[(2,6-dichlorophenyl)amino]6'-hydroxyphenylacetic acid.

EXAMPLE 41

Synthesis of 2-[(2,6-dichloro-3-benzyloxy-4-methoxyphenyl)amino]phenylacetic Acid In the manner described in example 22, 2,6-dichloro-3-benzyloxy-4-methoxydiphenylamine was used to yield 2-[(2,6-dichloro-3-benzyloxy-4-methoxyphenyl)amino] phenylacetic acid.

EXAMPLE 42

Synthesis of 2-[(2,6-dichloro-3-hydroxy-4-methoxyphenyl)amino]phenylacetic Acid

In the manner described in example 38, 2-[(2,6-dichloro-3-benzyloxy-4-methoxyphenyl)amino]phenylacetic acid was converted to 2-[(2,6-dichloro-3-hydroxy-4-methoxyphenyl)amino]phenylacetic acid.

EXAMPLE 43

Synthesis of 2-[(2,6-dichloro-4-methoxyphenyl) amino]5'-methoxyphenylacetic Acid In the manner described in example 22, 4-methoxy-2', 6'-dichloro-4'-methoxydiphenylamine is used to yield 2-[(2, 6-dichloro-4-methoxyphenyl)amino]5'-methoxyphenylacetic acid.

EXAMPLE 44

Synthesis of 2-[(2,6-dichloro-4-hydroxyphenyl) amino]5'-hydroxyphenylacetic Acid In the manner described in example 23, 2-[(2,6-dichloro-4-methoxyphenyl)amino]5'-methoxyphenylacetic acid was converted to 2-[(2,6-dichloro-4-hydroxyphenyl)amino]5'-hydroxyphenylacetic acid.

EXAMPLE 45

Synthesis of 2-[(2-methoxyphenyl)amino] phenylacetic Acid

In the manner described in example 3, 2-bromophenylacetic acid is condensed with o-anisidine to yield 2-[(2-methoxyphenyl)amino]phenylacetic acid.

EXAMPLE 46

Synthesis of 2-[(3-methoxyphenyl)amino] phenylacetic Acid

In the manner described in example 3, 2-bromophenylacetic acid is condensed with m-anisidine to yield 2-[(3-methoxyphenyl)amino]phenylacetic acid.

EXAMPLE 47

Synthesis of 2-[(4-methoxyphenyl)amino] phenylacetic Acid

In the manner described in example 3, 2-bromophenylacetic acid is condensed with p-anisidine to yield 2-[(4-methoxyphenyl)amino]phenylacetic acid.

EXAMPLE 48

Synthesis of 2-[(2-hydroxyphenyl)amino] phenylacetic Acid

In the manner described in example 23, 2-[(2-methoxyphenyl)amino]phenylacetic acid is converted to 2-[(2-hydroxyphenyl)amino]phenylacetic acid.

EXAMPLE 49

Synthesis of 2-[(3-hydroxyphenyl)amino]phenylacetic Acid

In the manner described in example 23, 2-[(3-methoxyphenyl)amino]phenylacetic acid is converted to 2-[(3-hydroxyphenyl)amino]phenylacetic acid.

EXAMPLE 50

Synthesis of 2-[(4-hydroxyphenyl)amino]phenylacetic Acid

In the manner described in example 23, 2-[(4-methoxyphenyl)amino]phenylacetic acid is converted to 2-[(4-hydroxyphenyl)amino]phenylacetic acid.

EXAMPLE 51

Synthesis of 2-[(3-chloro-4-methoxyphenyl)amino]phenylacetic Acid

In the manner described in example 3, 2-bromophenylacetic acid is condensed with 3-chloro-4-methoxyaniline to yield 2-[(3-chloro-4-methoxyphenyl)amino]phenylacetic acid.

EXAMPLE 52

Synthesis of 2-[(3-chloro-4-hydroxyphenyl)amino]phenylacetic Acid

In the manner described in example 23, 2-[(3-chloro-4-methoxyphenyl)amino]phenylacetic acid is converted to 2-[(3-chloro-4-hydroxyphenyl)amino]phenylacetic acid.

EXAMPLE 53

Synthesis of 2-[(2-methoxy-5-chlorophenyl)amino]phenylacetic Acid

In the manner described in example 3, 2-bromophenylacetic acid is condensed with 2-methoxy-5-chloroaniline to yield 2-[(2-methoxy-5-chlorophenyl)amino]phenylacetic acid.

EXAMPLE 54

Synthesis of 2-[(2-hydroxy-5-chlorophenyl)amino]phenylacetic Acid

In the manner described in example 23, 2-[(2-methoxy-5-chlorophenyl)amino]phenylacetic acid is converted to 2-[(2-hydroxy-5-chlorophenyl)amino]phenylacetic acid.

EXAMPLE 55

Synthesis of 2-[(3-methoxy-6-chlorophenyl)amino]phenylacetic Acid

In the manner described in example 3, 2-bromophenylacetic acid is condensed with 3-methoxy-6-chloroaniline to yield 2-[(3-methoxy-6-chlorophenyl)amino]phenylacetic acid.

EXAMPLE 56

Synthesis of 2-[(3-hydroxy-6-chlorophenyl)amino]phenylacetic Acid

In the manner described in example 23, 2-[(3-methoxy-6-chlorophenyl)amino]phenylacetic acid is converted to 2-[(3-hydroxy-6-chlorophenyl)amino]phenylacetic acid.

EXAMPLE 57

Synthesis of 2-[(2-methoxy-3-fluorophenyl)amino]phenylacetic Acid

In the manner described in example 3, 2-bromophenylacetic acid is condensed with 2-methoxy-3-fluoroaniline to yield 2-[(2-methoxy-3-fluorophenyl)amino]phenylacetic acid.

EXAMPLE 58

Synthesis of 2-[(2-hydroxy-3-fluorophenyl)amino]phenylacetic Acid

In the manner described in example 23, 2-[(2-methoxy-3-fluorophenyl)amino]phenylacetic acid is converted to 2-[(2-hydroxy-3-fluorophenyl)amino]phenylacetic acid.

EXAMPLE 59

Synthesis of 2-[(3-fluoro-4-methoxyphenyl)amino]phenylacetic Acid

In the manner described in example 3, 2-bromophenylacetic acid is condensed with 3-fluoro-4-methoxyaniline to yield 2-[(3-fluoro-4-methoxyphenyl)amino]phenylacetic acid.

EXAMPLE 60

Synthesis of 2-[(3-fluoro-4-hydroxyphenyl)amino]phenylacetic Acid

In the manner described in example 23, 2-[(3-fluoro-4-methoxyphenyl)amino]phenylacetic acid is converted to 2-[(3-fluoro-4-hydroxyphenyl)amino]phenylacetic acid.

EXAMPLE 61

Synthesis of 2-[(2-methoxy-4-nitrophenyl)amino]phenylacetic Acid

In the manner described in example 3, 2-bromophenylacetic acid is condensed with 2-methoxy-4-nitroaniline to yield 2-[(2-methoxy-4-nitrophenyl)amino]phenylacetic acid.

EXAMPLE 62

Synthesis of 2-[(2-hydroxy-4-nitrophenyl)amino]phenylacetic Acid

In the manner described in example 23, 2-[(2-methoxy-4-nitrophenyl)amino]phenylacetic acid is converted to 2-[(2-hydroxy-4-nitrophenyl)amino]phenylacetic acid.

EXAMPLE 63

Synthesis of 2-[(2-methoxy-5-nitrophenyl)amino]phenylacetic Acid

In the manner described in example 3, 2-bromophenylacetic acid is condensed with 2-methoxy-5-nitroaniline to yield 2-[(2-methoxy-5-nitrophenyl)amino]phenylacetic acid.

EXAMPLE 64

Synthesis of 2-[(2-hydroxy-5-nitrophenyl)amino]phenylacetic Acid

In the manner described in example 23, 2-[(2-methoxy-5-nitrophenyl)amino]phenylacetic acid is converted to 2-[(2-hydroxy-5-nitrophenyl)amino]phenylacetic acid.

EXAMPLE 65

Synthesis of 2-[(2-nitro-4-methoxyphenyl)amino]phenylacetic Acid

In the manner described in example 3, 2-bromophenylacetic acid is condensed with 2-nitro-4-methoxyaniline to yield 2-[(2-nitro-4-methoxyphenyl)amino]phenylacetic acid.

EXAMPLE 66

Synthesis of 2-[(2-nitro-4-hydroxyphenyl)amino]phenylacetic Acid

In the manner described in example 23, 2-[(2-nitro-4-methoxyphenyl)amino]phenylacetic acid is converted to 2-[(2-nitro-4-hydroxyphenyl)amino]phenylacetic acid

EXAMPLE 67

Synthesis of 2-[(2-nitro-4-ethoxyphenyl)amino]phenylacetic Acid

In the manner described in example 3, 2-bromophenylacetic acid is condensed with 2-nitro-4-ethoxyaniline to yield 2-[(2-nitro-4-ethoxyphenyl)amino]phenylacetic acid.

EXAMPLE 68

Synthesis of 2-[(3-methoxy-5-(trifluoromethyl)phenyl)amino]phenylacetic Acid

In the manner described in example 3, 2-bromophenylacetic acid is condensed with 3-methoxy-5-(trifluoromethyl)aniline to yield 2-[(3-methoxy-5-(trifluoromethyl)phenyl)amino]phenylacetic acid.

EXAMPLE 69

Synthesis of 2-[(3-hydroxy-5-(trifluoromethyl)phenyl)amino]phenylacetic Acid

In the manner described in example 23, 2-[(3-methoxy-5-(trifluoromethyl)phenyl)amino]phenylacetic acid is converted to 2-[(3-hydroxy-5-(trifluoromethyl)phenyl)amino]phenylacetic acid.

EXAMPLE 70

Synthesis of 2-[(2-ethylphenyl)amino]phenylacetic Acid

In the manner described in example 3, 2-bromophenylacetic acid is condensed with 2-ethylaniline to yield 2-[(2-ethylphenyl)amino]phenylacetic acid.

EXAMPLE 71

Synthesis of 2-[(3-ethylphenyl)amino]phenylacetic Acid

In the manner described in example 3, 2-bromophenylacetic acid is condensed with 3-ethylaniline to yield 2-[(3-ethylphenyl)amino]phenylacetic acid.

EXAMPLE 72

Synthesis of 2-[(4-ethylphenyl)amino]phenylacetic Acid

In the manner described in example 3, 2-bromophenylacetic acid is condensed with 4-ethylaniline to yield 2-[(4-ethylphenyl)amino]phenylacetic acid.

EXAMPLE 73

Synthesis of 2-[(2-bromophenyl)amino]phenylacetic Acid

In the manner described in example 3, 2-bromophenylacetic acid is condensed with 2-bromoaniline to yield 2-[(2-bromophenyl)amino]phenylacetic acid.

EXAMPLE 74

Synthesis of 2-[(3-bromophenyl)amino]phenylacetic Acid

In the manner described in example 3, 2-bromophenylacetic acid is condensed with 3-bromoaniline to yield 2-[(3-bromophenyl)amino]phenylacetic acid.

EXAMPLE 75

Synthesis of 2-[(4-bromophenyl)amino]phenylacetic Acid

In the manner described in example 3, 2-bromophenylacetic acid is condensed with 4-bromoaniline to yield 2-[(4-bromophenyl)amino]phenylacetic acid.

EXAMPLE 76

Synthesis of 2-[(2-fluorophenyl)amino]phenylacetic Acid

In the manner described in example 3, 2-bromophenylacetic acid is condensed with 2-fluoroaniline to yield 2-[(2-fluorophenyl)amino]phenylacetic acid.

EXAMPLE 77

Synthesis of 2-[(3-fluorophenyl)amino]phenylacetic Acid

In the manner described in example 3, 2-bromophenylacetic acid is condensed with 3-fluoroaniline to yield 2-[(3-fluorophenyl)amino]phenylacetic acid.

EXAMPLE 78

Synthesis of 2-[(4-fluorophenyl)amino]phenylacetic Acid

In the manner described in example 3, 2-bromophenylacetic acid is condensed with 4-fluoroaniline to yield 2-[(4-fluorophenyl)amino]phenylacetic acid.

EXAMPLE 79

Synthesis of 2-[(2-iodophenyl amino]phenylacetic Acid

In the manner described in example 3, 2-bromophenylacetic acid is condensed with 2-iodoaniline to yield 2-[(2-iodophenyl)amino]phenylacetic acid.

EXAMPLE 80

Synthesis of 2-[(3-iodophenyl)amino]phenylacetic Acid

In the manner described in example 3, 2-bromophenylacetic acid is condensed with 3-iodoaniline to yield 2-[(3-iodophenyl)amino]phenylacetic acid.

EXAMPLE 81

Synthesis of 2-[(4-iodophenyl)amino]phenylacetic Acid

In the manner described in example 3, 2-bromophenylacetic acid is condensed with 4-iodoaniline to yield 2-[(4-iodophenyl)amino]phenylacetic acid.

EXAMPLE 82

Synthesis of 2-[(2-nitrophenyl)amino]phenylacetic Acid

In the manner described in example 3, 2-bromophenylacetic acid is condensed with 2-nitroaniline to yield 2-[(2-nitrophenyl)amino]phenylacetic acid.

EXAMPLE 83

Synthesis of 2-[(3-nitrophenyl)amino]phenylacetic Acid

In the manner described in example 3, 2-bromophenylacetic acid is condensed with 3-nitroaniline to yield 2-[(3-nitrophenyl)amino]phenylacetic acid.

EXAMPLE 84

Synthesis of 2-[(4-nitrophenyl)amino]phenylacetic Acid

In the manner described in example 3, 2-bromophenylacetic acid is condensed with 4-nitroaniline to yield 2-[(4-nitrophenyl)amino]phenylacetic acid.

EXAMPLE 85

Synthesis of 2-[(3,4-difluorophenyl)amino] phenylacetic Acid

In the manner described in example 3, 2-bromophenylacetic acid is condensed with 3,4-difluoroaniline to yield 2-[(3,4-difluorophenyl)amino] phenylacetic acid.

EXAMPLE 86

Synthesis of 2-[(3,5-difluorophenyl)amino] phenylacetic Acid

In the manner described in example 3, 2-bromophenylacetic acid is condensed with 3,5-difluoroaniline to yield 2-[(3,5-difluorophenyl)amino] phenylacetic acid.

EXAMPLE 87

Synthesis of 2-[(2,5-difluorophenyl)amino] phenylacetic Acid

In the manner described in example 3, 2-bromophenylacetic acid is condensed with 2,5-difluoroaniline to yield 2-[(2,5-difluorophenyl)amino] phenylacetic acid.

EXAMPLE 88

Synthesis of 2-[(2,3-difluorophenyl)amino] phenylacetic Acid

In the manner described in example 3, 2-bromophenylacetic acid is condensed with 2,3-difluoroaniline to yield 2-[(2,3-difluorophenyl)amino] phenylacetic acid.

EXAMPLE 89

Synthesis of 2-[(2,4-dibromophenyl)amino] phenylacetic Acid

In the manner described in example 3, 2-bromophenylacetic acid is condensed with 2,4-dibromoaniline to yield 2-[(2,4-dibromophenyl)amino] phenylacetic acid.

EXAMPLE 90

Synthesis of 2-[(2,5-dibromophenyl)amino] phenylacetic Acid

In the manner described in example 3, 2-bromophenylacetic acid is condensed with 2,5-dibromoaniline to yield 2-[(2,5-dibromophenyl)amino] phenylacetic acid.

EXAMPLE 91

Synthesis of 2-[(2,6-dibromophenyl)amino] phenylacetic Acid

In the manner described in example 3, 2-bromophenylacetic acid is condensed with 2,6-dibromoaniline to yield 2-[(2,6-dibromophenyl)amino] phenylacetic acid.

EXAMPLE 92

Synthesis of 2-[(3-chloro-4-fluorophenyl)amino] phenylacetic Acid

In the manner described in example 3, 2-bromophenylacetic acid is condensed with 3-chloro-4-fluoroaniline to yield 2-[(3-chloro-4-fluorophenyl)amino] phenylacetic acid.

EXAMPLE 93

Synthesis of 2-[(2-fluoro-4-chlorophenyl)amino] phenylacetic Acid

In the manner described in example 3, 2-bromophenylacetic acid is condensed with 2-fluoro-4-chloroaniline to yield 2-[(2-fluoro-4-chlorophenyl)amino] phenylacetic acid.

EXAMPLE 94

Synthesis of 2-[(3-nitro-4-chlorophenyl)amino] phenylacetic Acid

In the manner described in example 3, 2-bromophenylacetic acid is condensed with 3-nitro-4-chloroaniline to yield 2-[(3-nitro-4-chlorophenyl)amino] phenylacetic acid.

EXAMPLE 95

Synthesis of 2-[(2-fluoro-5-nitrophenyl)amino] phenylacetic Acid

In the manner described in example 3, 2-bromophenylacetic acid is condensed with 2-fluoro-5-nitroaniline to yield 2-[(2-fluoro-5-nitrophenyl)amino] phenylacetic acid.

EXAMPLE 96

Synthesis of 2-[(3-nitro-4-fluorophenyl)amino] phenylacetic Acid

In the manner described in example 3, 2-bromophenylacetic acid is condensed with 3-nitro-4-fluoroaniline to yield 2-[(3-nitro-4-fluorophenyl)amino] phenylacetic acid.

EXAMPLE 97

Synthesis of 2-[(2-fluoro-4-iodophenyl)amino]phenylacetic Acid

In the manner described in example 3, 2-bromophenylacetic acid is condensed with 2-fluoro-4-iodoaniline to yield 2-[(2-fluoro-4-iodophenyl)amino]phenylacetic acid.

EXAMPLE 98

Synthesis of 2-[(3,5-dinitrophenyl)amino]phenylacetic Acid

In the manner described in example 3, 2-bromophenylacetic acid is condensed with 3,5-dinitroaniline to yield 2-[(3,5-dinitrophenyl)amino]phenylacetic acid.

EXAMPLE 99

Synthesis of 2-[(2-fluoro-4-bromophenyl)amino]phenylacetic Acid

In the manner described in example 3, 2-bromophenylacetic acid is condensed with 2-fluoro-4-bromoaniline to yield 2-[(2-fluoro-4-bromophenyl)amino]phenylacetic acid.

EXAMPLE 100

Synthesis of 2-[(2,3,4-trifluorophenyl)amino]phenylacetic Acid

In the manner described in example 3, 2-bromophenylacetic acid is condensed with 2,3,4-trifluoroaniline to yield 2-[(2,3,4-trifluorophenyl)amino]phenylacetic acid.

EXAMPLE 101

Synthesis of 2-[(3,4,5-trichlorophenyl)amino]phenylacetic Acid

In the manner described in example 3, 2-bromophenylacetic acid is condensed with 3,4,5-trichloroaniline to yield 2-[(3,4,5-trichlorophenyl)amino]phenylacetic acid.

EXAMPLE 102

Synthesis of 2-[(2,4,5-triflourophenyl)amino]phenylacetic Acid

In the manner described in example 3, 2-bromophenylacetic acid is condensed with 2,4,5-triflouroaniline to yield 2-[(2,4,5-triflourophenyl)amino]phenylacetic acid.

EXAMPLE 103

Synthesis of 2-[(2,3,4,6-tetrafluorophenyl)amino]phenylacetic Acid

In the manner described in example 3, 2-bromophenylacetic acid is condensed with 2,3,4,6-tetrafluoroaniline to yield 2-[(2,3,4,6-tetrafluorophenyl)amino]phenylacetic acid.

EXAMPLE 104

Synthesis of 2-[(3-methyl-4-bromophenyl)amino]phenylacetic Acid

In the manner described in example 3, 2-bromophenylacetic acid is condensed with 3-methyl-4-bromoaniline to yield 2-[(3-methyl-4-bromophenyl)amino]phenylacetic acid.

EXAMPLE 105

Synthesis of 2-[(3-bromo-4-methylphenyl)amino]phenylacetic Acid

In the manner described in example 3, 2-bromophenylacetic acid is condensed with 3-bromo-4-methylaniline to yield 2-[(3-bromo-4-methylphenyl)amino]phenylacetic acid.

EXAMPLE 106

Synthesis of 2-[(3-fluoro-4-methylphenyl)amino]phenylacetic Acid

In the manner described in example 3, 2-bromophenylacetic acid is condensed with 3-fluoro-4-methylaniline to yield 2-[(3-fluoro-4-methylphenyl)amino]phenylacetic acid.

EXAMPLE 107

Synthesis of 2-[(3-methylmercaptophenyl)amino]phenylacetic Acid

In the manner described in example 3, 2-bromophenylacetic acid is condensed with 3-methylmercaptoaniline to yield 2-[(3-methylmercaptophenyl)amino]phenylacetic acid.

EXAMPLE 108

Synthesis of 2-[(4-methylmercaptophenyl)amino]phenylacetic Acid

In the manner described in example 3, 2-bromophenylacetic acid is condensed with 4-methylmercaptoaniline to yield 2-[(4-methylmercaptophenyl)amino]phenylacetic acid.

EXAMPLE 109

Synthesis of 2-[(3-nitro-4-methylphenyl)amino]phenylacetic Acid

In the manner described in example 3, 2-bromophenylacetic acid is condensed with 3-nitro-4-methylaniline to yield 2-[(3-nitro-4-methylphenyl)amino]phenylacetic acid.

EXAMPLE 110

Synthesis of 2-[(3,5-methoxyphenyl)amino]phenylacetic Acid

In the manner described in example 3, 2-bromophenylacetic acid is condensed with 3,5-methoxyaniline to yield 2-[(3,5-methoxyphenyl)amino]phenylacetic acid.

EXAMPLE 111

Synthesis of 2-[(3,5-hydroxyphenyl)amino]phenylacetic Acid

In the manner described in example 23, 2-[(3,5-methoxyphenyl)amino]phenylacetic acid is converted to 2-[(3,5-hydroxyphenyl)amino]phenylacetic acid

EXAMPLE 112

Synthesis of 2-[(4-propylphenyl)amino]phenylacetic Acid

In the manner described in example 3, 2-bromophenylacetic acid is condensed with 4-propylaniline to yield 2-[(4-propylphenyl)amino]phenylacetic acid.

EXAMPLE 113

Synthesis of 2-[(4-isopropylphenyl)amino] phenylacetic Acid

In the manner described in example 3, 2-bromophenylacetic acid is condensed with 4-isopropylaniline to yield 2-[(4-isopropylphenyl)amino] phenylacetic acid.

EXAMPLE 114

Synthesis of 2-[(3,4,5-trimethoxyphenyl)amino] phenylacetic Acid

In the manner described in example 3, 2-bromophenylacetic acid is condensed with 3,4,5-trimethoxyaniline to yield 2-[(3,4,5-trimethoxyphenyl) amino]phenylacetic acid.

EXAMPLE 115

Synthesis of 2-[(3,4,5-trihydroxyphenyl)amino] phenylacetic Acid

In the manner described in example 23, 2-[(3,4,5-trimethoxyphenyl)amino]phenylacetic acid is converted to 2-[(3,4,5-trihydroxyphenyl)amino]phenylacetic acid.

EXAMPLE 116

Synthesis of 2-[(4-butylphenyl)amino]phenylacetic Acid

In the manner described in example 3, 2-bromophenylacetic acid is condensed with 4-butylaniline to yield 2-[(4-butylphenyl)amino]phenylacetic acid.

EXAMPLE 117

Synthesis of 2-[(4-butoxyphenyl)amino] phenylacetic Acid

In the manner described in example 3, 2-bromophenylacetic acid is condensed with 4-butoxyaniline to yield 2-[(4-butoxyphenyl)amino] phenylacetic acid.

EXAMPLE 118

Synthesis of 2-[(4-pentylphenyl)amino]phenylacetic Acid

In the manner described in example 3, 2-bromophenylacetic acid is condensed with 4-pentylaniline to yield 2-[(4-pentylphenyl)amino]phenylacetic acid.

EXAMPLE 119

Synthesis of 2-[(4-pentyloxyphenyl)amino] phenylacetic Acid

In the manner described in example 3, 2-bromophenylacetic acid is condensed with 4-pentyloxyaniline to yield 2-[(4-pentyloxyphenyl)amino] phenylacetic acid.

EXAMPLE 120

Anti-Glycation Activity of 2-(phenylamino) phenylacetic Acids

Human albumin (10 mg/ml) was incubated for 48–144 hours at 37° C. in the presence of 0–50 mM glucose in buffered saline, without or with the test compound in varying concentrations (1–1000 $\mu$M). After dialysis to remove free glucose and compound, the amount of glycated albumin formed was determined by enzyme-linked immunosorbent assay using the monoclonal antibodies known to specifically react with Amadori-glucose adducts in glycated albumin and to be unreactive with the nonglycated protein. The presence of glucose in the incubations promotes the nonenzymatic glycation of albumin, and the performance of paired incubations allows comparison of the amount of glycated albumin formed under control (0 glucose), stimulated (25–50 mM glucose), and inhibited (compound plus glucose) conditions. From these data, the $IC_{50}$ (concentration required for 50% inhibition) for glycation inhibition was calculated. The $IC_{50}$ ($\mu$M) for inhibition of glycation by a representative sample of 2-(phenylamino)phenylacetic acid compounds is shown in Table 2.

TABLE 2

Prevention of Albumin Glycation by 2-(phenylamino)phenylacetic acids

| Example # | Glycation Inhibition $IC_{50}$ ($\mu$m) |
| --- | --- |
| 3 | 500 |
| 4 | 10 |
| 5 | 50 |
| 6 | 11 |
| 8 | 63 |
| 10 | 6.3 |
| 11 | 2.5 |
| 13 | 112 |

EXAMPLE 121

Cyclo-oxygenase Inhibitory Activity of 2-(phenylamino)phenylacetic Acids

Cellular homogenates of bovine seminal vesicles were incubated with arachidonic acid and the production of prostaglandins was monitored. The effect of test compound on the conversion of arachidonic acid to prostaglandin $E_2$ was measured after incubation for 1–30 minutes in buffer containing the cofactors hematin and phenol. Compounds were tested in varying concentration (1–1000 $\mu$M) and the data used to calculate the $IC_{50}$ for cyclo-oxygenase inhibition. The cyclo-oxygenase-inhibitory activity of representative 2-(phenylamino)phenylacetic acids is presented in Table 3.

TABLE 3

COX Inhibitory Activity of 2-(phenylamino) phenylacetic acids.

| Example # | COX Inhibition IC50 ($\mu$M) |
| --- | --- |
| 3 | 288 |
| 4 | 42 |
| 5 | 600 |
| 6 | 98 |
| 8 | 71 |
| 10 | 1 |
| 11 | 141 |
| 13 | 6 |

EXAMPLE 122

Relative Anti-Glycation Versus Cyclo-oxygenase Inhibitory Activity

It was determined from the ratio of 6.3 of the $IC_{50}$ of glycation to cyclo-oxygenase inhibitory activities of 2-(2,6- dichlorophenylainino)phenylacetic acid that an antiglycation: cyclo-oxygenase inhibition $IC_{50}$ ratio less than 2 would provide a favorable therapeutic profile in which therapeutic concentrations achieving significant antiglycation activity would have insignificant cyclo-oxygenase inhibitory activity. The anti-glycation: cyclo-oxygenase inhibition ratio of representative 2-(phenylamino) phenylacetic acids is shown in Table 4.

TABLE 4

| Example # | Antiglycation $IC_{50}$ versus COX Inhibition $IC_{50}$ |
|---|---|
| 3 | 0.54 |
| 4 | 0.24 |
| 5 | 0.08 |
| 6 | 0.11 |
| 8 | 0.90 |
| 10 | 6.3 |
| 11 | 0.02 |
| 13 | 19.0 |

EXAMPLE 123

Prevention of Albumin Glycation in vivo by Administration of 2-(phenylamino)phenylacetic acids Mice were administered 3 to 10 mg/kg of 2-(2-chlorophenyl amino)phenylacetic acid or 2-(3-chlorophenylamino)phenylacetic acid [or 2–2,6-dichlorophenylamino-phenylacetic acid], given in divided doses by intraperitoneal injection for 5 days.

| | Glycated Albumin ($\mu$g/ml) | | |
|---|---|---|---|
| Dose | Pre-Treatment | Post-Treatment | Percent Change |
| 2-(3-chlorophenylamino)phenylacetic acid | | | |
| 5 mg/kg/day | 854 | 697 | −18.4 |
| 10 mg/kg/day | 647 | 352 | −45.6 |
| 2-(2-chlorophenylamino)phenylacetic acid | | | |
| 5 mg/kg/day | 741 | 500 | −32.5 |
| 10 mg/kg/day | 815 | 426 | −47.7 |

Example 124

Lowering Glycated Albumin with 2-(phenylamino) phenyl Acetic Acid Compounds Ameliorates Glycation-related Pathology Mice were treated for 8 weeks with [6 mg/kg/day of 2-(2,6-dichlorophenylamino)phenylacetic acid] 10 mg/kg/day of 2-(3-chlorophenylamino)phenylacetic acid in divided doses.

| | Urine protein $\mu$g/24 hrs |
|---|---|
| Initiation | 7.6 |
| Termination | 2.7 |

EXAMPLE 125

Therapeutic Composition/treatment

A. Tablet

A typical tablet contains 2-[(2-chlorophenyl)amino] phenylacetic acid (100 mg), pregelatinized starch USP (82 mg), microcrystalline cellulose (82 mg), and magnesium stearate (1 mg). In like manners, for example, 2-[(3-chlorophenyl)amino]phenylacetic acid can be formulated in place of 2-[(2-chlorophenyl)amino]phenyl acetic acid.

B. Liquid

A typical liquid contains 2-[(2-chlorophenyl)amino] phenylacetic acid (50 mg), sodium phosphate dibasic (50 mg), ethyl alcohol (0.5 ml), water (5 ml) and sweetening and/or flavoring agents. Similarly, other formulations can be made by substituting, for example, 2-[(3-chlorophenyl) amino]phenylacetic acid for 2-[(2-chlorophenyl)amino] phenylacetic acid.

C. Injection

A typical injectable formulation contains 2-[(2-chlorophenyl)amino]phenylacetic acid (25 mg) sodium phosphate dibasic (11.4 mg), benzyl alcohol (0.01 ml) and water for injection (1 ml). Similarly, this formulation can be prepared employing, for example, 2-[(3 chlorophenyl) amino]phenylacetic acid in place of 2-[(2 chlorophenyl) amino]phenylacetic acid.

D. Suppositories

Typical suppository formulations can contain 2-[(2 chlorophenyl)amino]phenylacetic acid (50 mg) butylated hydroxyanisol (0.1–1.0 mg), disodium calcium edetate (0.25–0.50 mg), and polyethyleneglycol (775–1600 mg). Other suppository formulations can be made by substituting, for example, 2-[(3-chlorophenyl)amino]phenylacetic acid for 2-[(2-chlorophenyl)amino]phenylacetic acid and by substituting, for example, butylated hydroxytoluene (0.04–0.08 mg) for the disodium calcium edetate and a hydrogenated vegetable oil (678–1400 mg), such as Suppocire L, Wecobee F S, Wecobee M, Witepsols, and the like, for the polyethylene glycol.

I claim:

1. A compound selected from those having the following structure:

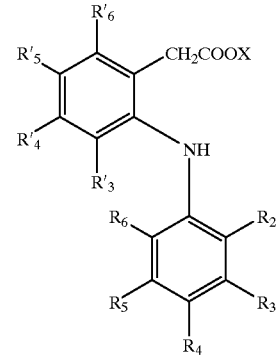

wherein: $R'_3$, $R'_4$, $R'_5$, $R'_6$, $R_2$, $R_3$, $R_4$, $R_5$ and $R_6$ are the same or different and are hydrogen, chlorine, bromine, fluorine, iodine, ethyl, ethoxy, methoxy, hydroxy, phosphate, sulfate, nitrate, amino or ethyl, and $R_2$ and $R_6$ are both not chlorine when $R'_3$, $R'_4$, $R'_5$, $R'_6$, $R_3$, $R_4$ and $R_5$ are hydrogen; X is hydrogen, sodium, potassium or lithium.

2. A compound of claim 1 that inhibits the formation of glucose adducts on albumin.

3. A compound of claim 1 that inhibits the formation of glucose adducts on one or more residues of albumin as defined by a monoclonal antibody produced by cell line ATCC HB9596.

4. A compound of claim 3 that is 2-[(3-chlorophenyl)amino]phenylacetic acid.

5. A process for preparing a compound of claim 1 comprising the steps of reacting a phenylamine of the formula.

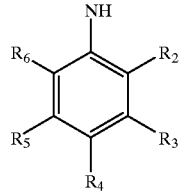

wherein $R_2$, $R_3$, $R_4$, $R_5$, $R_6$ may include suitable protection of any reactive group; with a phenylacetic acid of the formula:

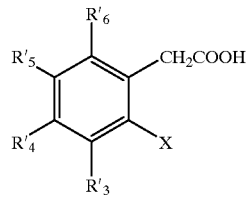

wherein $R'_3$, $R'_4$, $R'_5$, and $R'_6$ may include suitable protection of any reactive group and where X is chlorine, bromine, iodine or a sulfonyloxy derivative in the presence of neutralizing agent and copper catalyst followed by removal of the protecting group, if necessary, to form the desired product, and, if desired, preparing a salt thereof by conventional means.

6. A process for preparing a compound of claim 2 comprising the steps of reacting a phenylamine of the formula:

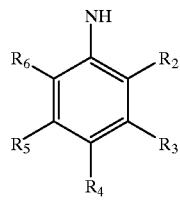

wherein:
$R_2$, $R_3$, $R_4$, $R_5$, $R_6$ may include suitable protection of any reactive group; with a phenylacetic acid of the formula:

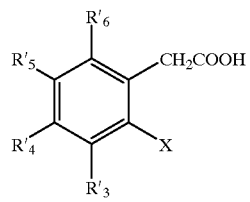

wherein:
$R'_3$, $R'_4$, $R'_5$, $R'_6$ may include suitable protection of any reactive group and where X is chlorine, bromine, iodine or a sulfonyloxy derivative in the presence of neutralizing agent and copper catalyst followed by removal of the protecting group, if necessary, to form the desired product, and, if desired, preparing a salt thereof by conventional means.

7. A process for preparing a compound of claim 3 comprising the steps of reacting a phenylamine of the formula:

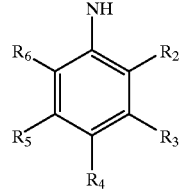

wherein:
$R_2$, $R_3$, $R_4$, $R_5$, $R_6$ may include suitable protection of any reactive group; with a phenylacetic acid of the formula:

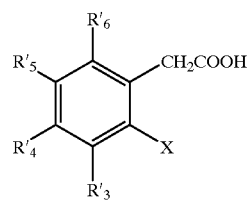

wherein:
$R'_3$, $R'_4$ and $R'_5$ and $R'_6$ may include suitable protection of any reactive group and where X is chlorine, bromine, iodine or a sulfonyloxy derivative in the presence of neutralizing agent and copper catalyst followed by removal of the protecting group, if necessary, to form the desired product, and, if desired, preparing a salt thereof by conventional means.

8. A process for preparing a compound of claim 4 comprising the steps of reacting a phenylamine of the formula:

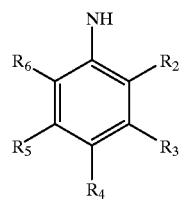

wherein:
$R_2$, $R_3$, $R_5$, $R_6$ may include suitable protection of any reactive group; with a phenylacetic acid of the formula:

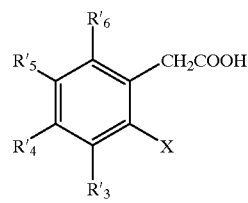

wherein:
$R'_3$, $R'_4$, $R'_5$ and $R'_6$ may include suitable protection of any reactive group X is chlorine, bromine, iodine or a sulfonyloxy derivative in the presence of neutralizing agent an copper catalyst followed by removal of the protecting group, if necessary, to form the desired product, and, if desired, preparing a salt thereof by conventional means.

9. A method that identifies compounds that, by binding to specific sites in albumin and thereby rendering pathophysiologically important glycatable sites inaccessible to reaction with carbohydrate, inhibits the formation of glucose adducts on albumin, wherein said albumin containing glucose adducts has pathophysiologic effects in living organisms and wherein said compounds can inhibit the formation of glucose adducts on albumin at concentrations of 300 micromolar or less.

* * * * *